United States Patent [19]

Fikentscher et al.

[11] Patent Number: 4,652,669
[45] Date of Patent: Mar. 24, 1987

[54] 2-(1-HYDROXYCARBALKOXYMETHYL)-ACRYLONITRILES AND 2-(1-HYDROXYCARBALKOXYMETHYL)-ACRYLATES AND THEIR PREPARATION

[75] Inventors: Rolf Fikentscher, Ludwigshafen; Erwin Hahn, Heidelberg; Alexander Kud, Enkenbach-Alsenborn; Alfred Oftring, Ludwigshafen, all of Fed. Rep. of Germany

[73] Assignee: BASF Aktiengesellschaft, Ludwigshafen, Fed. Rep. of Germany

[21] Appl. No.: 804,121

[22] Filed: Dec. 3, 1985

[30] Foreign Application Priority Data

Dec. 4, 1984 [DE] Fed. Rep. of Germany ....... 3444097

[51] Int. Cl.$^4$ ........................................... C07C 121/30
[52] U.S. Cl. .................................... 558/441; 558/371; 560/181
[58] Field of Search ................ 558/441, 371; 560/181; 568/840 B

[56] References Cited

U.S. PATENT DOCUMENTS 3,499,024  3/1970  Morita et al. ................ 560/181 UX
3,743,669  7/1973  Hillman et al. ........................ 560/64

OTHER PUBLICATIONS

Garbers, et al; J. Chem. Soc., Perkin Trans. I, (1973), pp. 2016–2019.
Tetrahedron Letters, vol. 25, No. 12, pp. 1303–1306, (1984), Papageorgiou et al, Synthesis of Potentially Allergenic Chiral Alpha–(Hydroxyalkyl)Acrylates.

Primary Examiner—Joseph Paul Brust
Attorney, Agent, or Firm—Oblon, Fisher, Spivak, McClelland & Maier

[57] ABSTRACT 2-(1-Hydroxycarbalkoxymethyl)-acrylonitriles and 2-(1-hydroxycarbalkoxymethyl)-acrylates are prepared by a process in which an acrylonitrile or an acrylate is reacted with a glyoxylate in an aqueous medium at a pH greater than or equal to 6, in the presence of a tertiary amine as a catalyst.

2 Claims, No Drawings

2-(1-HYDROXYCARBALKOXYMETHYL)-ACRYLONITRILES AND 2-(1-HYDROXYCARBALKOXYMETHYL)-ACRYLATES AND THEIR PREPARATION

U.S. Pat. No. 3,743,669 discloses the preparation of 2-(1-hydroxyalkyl)-acrylonitriles and of 2-(1-hydroxyalkyl)-acrylates of the general formula

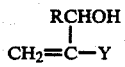
$$\text{CH}_2=\overset{\text{RCHOH}}{\underset{|}{\text{C}}}-\text{Y} \qquad \text{(III)}$$

where Y is, inter alia, —CN or

$$-\underset{\overset{\|}{\text{O}}}{\text{C}}-\text{OR}^1$$

and R and $R^1$ are each alkyl or aryl. The compounds of the formula III are prepared by reacting acrylonitrile or an acrylate of the formula $\text{CH}_2=\text{CH}-\text{Y}$ with an aldehyde of the formula RCHO where Y and R have the meanings stated for formula III, in the presence of a tertiary amine as a catalyst, at from 0° to 200° C.

It is an object of the present invention to provide compounds which, in addition to a double bond, contain further functional groups in the molecule. It is a further object of the present invention to provide a process for the preparation of the novel compounds.

We have found that this object is achieved, in accordance with the invention, by compounds of the formula

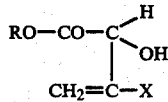
$$\text{RO}-\text{CO}-\underset{\underset{\text{CH}_2=\text{C}-\text{X}}{|}}{\overset{\overset{\text{H}}{|}}{\text{C}}}\underset{\text{OH}}{\overset{}{\diagdown}} \qquad \text{(I)}$$

where R is $C_1$-$C_{18}$-alkyl, X is —CN or

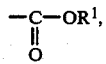
$$-\underset{\overset{\|}{\text{O}}}{\text{C}}-\text{OR}^1,$$

$R^1$ is $C_1$-$C_{18}$-alkyl, —$(CH_2)_n$—OH,

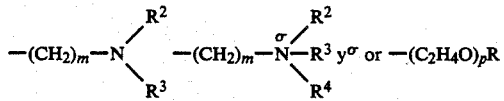

$R^2$ and $R^3$ are each —$CH_3$ or —$C_2H_5$, $R^4$ is —H, —$CH_3$, —$C_2H_5$ or

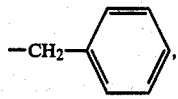

n is from 2 to 4, m is from 2 to 5, p is from 1 to 80 and $Y^-$ is $Cl^-$, $Br^-$, $SO_4^{2-}$, $PO_4^{3-}$, $CH_3OSO_3^-$, $C_2H_5OSO_3^-$, $CH_3COO^-$ or $HCOO^-$.

The compounds of the formula I are prepared by a process in which a compound of the formula

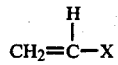
$$\text{CH}_2=\overset{\overset{\text{H}}{|}}{\text{C}}-\text{X} \qquad \text{(II)}$$

where X has the meanings stated for formula I, is reacted with a glyoxylate of the formula $$\text{RO}-\text{CO}-\text{CHO} \qquad \text{(III)}$$

where R is $C_1$-$C_{18}$-alkyl, in the presence of a tertiary amine as a catalyst.

Suitable compounds of the formula II are acrylonitrile and acrylates. In formula II, X can be —CN or

$$-\underset{\overset{\|}{\text{O}}}{\text{C}}-\text{OR}^1,$$

where $R^1$ is $C_1$-$C_{18}$-alkyl, —$(CH_2)_n$—OH,

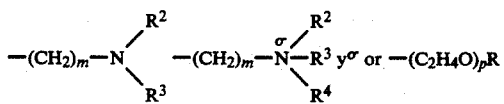

R is $C_1$-$C_{18}$-alkyl, $R^2$ and $R^3$ are each —$CH_3$ or $C_2H_5$, $R^4$ is —H, —$CH_3$, —$C_2H_5$,

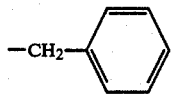

n is from 2 to 4, m is from 2 to 5, p is from 1 to 80 and $Y^-$ is $Cl^-$, $Br^-$, $SO_4^{2-}$, $PO_4^{3-}$, $CH_3OSO_3^-$, $C_2H_5OSO_3^-$, $CH_3COO^-$ or $HCOO^-$.

Examples of $C_1$-$C_{18}$-alkyl acrylates are methyl acrylate, ethyl acrylate, n-propyl acrylate, isopropyl acrylate, n-butyl acrylate, isobutyl acrylate, tert.-butyl acrylate, n-octyl acrylate, isooctyl acrylate, 2-ethylhexyl acrylate, cyclopentyl acrylate, cyclohexyl acrylate, lauryl acrylate, palmityl acrylate and stearyl acrylate. Formula II also embraces hydroxyethyl acrylate, hydroxypropyl acrylate and hydroxybutyl acrylate, where those hydroxyalkyl acrylates which are derived from $C_3$- and $C_4$-glycols can be prepared by esterification of all possible isomeric glycols, or mixtures of these, with acrylic acid, as well as dimethylaminoethyl acrylate, diethylaminoethyl acrylate, dimethylaminopropyl acrylate, diethylaminopropyl acrylate, dimethylaminobutyl acrylate, diethylaminobutyl acrylate, dimethylaminoneopentyl acrylate, diethylaminoneopentyl acrylate and the neutralized and quaternized dialkylaminoalkyl acrylates. Examples of suitable quaternization agents are dimethyl sulfate, diethyl sulfate, methyl chloride, ethyl chloride, methyl bromide, ethyl bromide and benzyl chloride. The salts of the dimethylaminoalkyl acrylates are obtained by neutralization with hydrochloric acid, hydrobromic acid, sulfuric acid, phosphoric acid or saturated carboxylic acid, such as formic acid or acetic acid. Other suitable compounds of the formula II are polyethoxyalkyl esters of acrylic acid which contain from 1 to 80, preferably from 3 to 30, ethoxy groups, e.g. methoxyethyl acrylate, ethoxyethyl acrylate and lauryloxytrioxyethyl acrylate. Preferably used compounds of the formula II are acrylonitrile, methyl acrylate, ethyl acrylate, 2-ethylhexyl acrylate, hydroxyethyl acrylate and hydroxybutyl acrylate.

The compounds of the formula II are reacted with glyoxylates of the formula III at from 0° to 150° C., preferably from 0° to 70° C., at a pH of from 7 to 13, in the presence of a tertiary amine as a catalyst. The pH of the reaction mixture can be from 7 to 13 and is preferably from 8 to 10, and is established by adding the tertiary amine which acts as a catalyst, and, if required, another base, such as sodium hydroxide solution, potassium hydroxide solution, sodium carbonate, potassium carbonate or calcium hydroxide. In the glyoxylates of the formula III, R can be $C_1$–$C_{18}$-alkyl. Examples of suitable glyoxylates are methyl glyoxylate, ethyl glyoxylate, n-propyl glyoxylate, isopropyl glyoxylate, butyl glyoxylate, 2-ethylhexyl glyoxylate and stearyl glyoxylate.

The reaction can be carried out in the absence of a diluent, i.e. using a pure substance, or in an inert solvent. Examples of suitable inert solvents are ethers, such as diethyl ether, dioxane, tetrahydrofuran, dimethylglycol ether, diethylglycol ether, methylglycol, ethylglycol or polyglycol ethers, as well as acetonitrile, aliphatic and aromatic hydrocarbons (e.g. pentane, hexane, cyclohexane, isooctane, n-octane, dodecane, toluene, xylene and tetralin), chlorohydrocarbons (e.g. dichloromethane, carbon tetrachloride, trichloroethane and tetrachloroethane), methyl ethyl ketone, acetone and water. In some cases, it may be more advantageous to use a solvent mixture than an individual solvent.

The reaction is preferably carried out in a homogeneous mixture and in the absence of an inert solvent. If the acrylate and glyoxylate used are very poorly soluble in water, it is advisable to carry out the reaction in the presence of a solvent which is inert to the reactants and is miscible with the latter and with water. As much as 1000, preferably from 10 to 200, parts by weight of an inert solvent may be used per 100 parts by weight of the mixture of the compounds of the formulae II and III.

The reaction is effected in the presence of a tertiary amine, and either an open-chain aliphatic amine or a cyclic tertiary amine may be used. Examples of these are trimethylamine, triethylamine, tri-n-propylamine, triisopropylamine, tributylamine, triisobutylamine, tri-n-pentylamine, N-methyldiisopropylamine, N,N-diethylisopropylamine, N,N-dimethylethylamine, N,N-dimethylisopropylamine, tri-2-ethylhexylamine, N-methyldiethylamine, N,N-dimethyl-n-propylamine, N,N-dimethyl-n-butylamine, N,N-dimethylisobutylamine, N,N-dimethyl-(2-ethylhexyl)amine, N,N-diisopropyl-(2-ethylhexyl)-amine, N,N-di-n-butyl-(2-ethylhexyl)-amine, N-methyldi-(2-ethylhexyl)amine, N-n-butyldi-(2-ethylhexyl)-amine, N-isobutyldi(2-ethylhexyl)-amine, 1,1-diazabicyclo[2.2.2]octane, pyrrocoline and quinolidine. From 0.1 to 10, preferably from 3 to 8, parts by weight of a tertiary amine are used per 100 parts by weight of the mixture of the compounds of the formulae II and III. The reaction is preferably carried out in the presence of 1,4-diazabicyclo[2.2.2]octane, pyrrocoline or quinolidine. As a rule, the compounds of the formulae II and III are reacted in equimolar amounts. For technical reasons, however, it may also be necessary to use one or other of the components in excess. For example, it is possible to vary the molar ratio of glyoxylate to the compound of the formula II in the range from 20:1 to 1:2, preferably from 5:1 to 0.75:1. The reaction is usually carried out under atmospheric pressure, although reduced pressure or superatmospheric pressure may also be employed. Superatmospheric pressure is necessary in particular when the reaction is carried out at above 100° C.

The products prepared by the novel process, i.e. 2-(1-hydroxycarbalkoxymethyl)-acrylonitriles and 2-(1-hydroxycarbalkoxymethyl)-acrylates of formula I above, are useful intermediates which are suitable, for example, as monomers for the preparation of polymers.

EXAMPLE 1

102 g (1 mole) of ethyl glyoxylate, 86 g (1 mole) of methyl acrylate and 7 g (0.062 mole) of 1,4-diazabicyclo[2.2.2]octane (abbreviated to DABCO below) are stirred vigorously for 48 hours in a 2 l three-necked flask in a nitrogen atmosphere at 50° C. Thereafter, the volatile components are removed under reduced pressure from a water pump, the residue is taken up with 250 ml of diethyl ether, the resulting solution is washed with 60 ml of 8% strength aqueous hydrochloric acid and then 100 ml of water, the organic phase is dried over sodium sulfate, the ether is removed and the residue is distilled under reduced pressure. 149 g (79% of theory) of methyl 2-(1-hydroxycarbethoxymethyl)-acrylate are obtained as a colorless liquid of boiling point 96°–100° C. under 0.4 mbar.

EXAMPLE 2

26 g (0.2 mole) of n-butyl glyoxylate, 25.6 g (0.2 mole) of isobutyl acrylate and 2 g (17.8 millimoles) of DABCO are heated for 27 hours at 50° C., while stirring. Thereafter, volatile components are removed under reduced pressure, the oily residue is taken up in 200 ml of diethyl ether, the solution is washed with 50 ml of 10% strength aqueous hydrochloric acid and with 50 ml of water and then dried over sodium sulfate, and the solvent is distilled off. 34 g (66% of theory) of isobutyl 2-(1-hydroxycarbobutoxymethyl)-acrylate remain as a yellow oil.

EXAMPLE 3

44 g (0.5 mole) of methyl glyoxylate, 43 g (0.5 mole) of methyl acrylate and 4 g (35.7 millimoles) of DABCO are stirred vigorously for 48 hours at 25° C. Volatile components are distilled off under reduced pressure from a water pump, after which the oily residue is taken up in 200 ml of diethyl ether, the resulting solution is washed with 50 ml of 8% strength hydrochloric acid and with 75 ml of water, the organic phase is dried over sodium sulfate, the solvent is removed under reduced pressure from an oil pump and the residue is then subjected to fractional distillation. 64 g (74% of theory) of methyl 2-(hydroxycarbomethoxymethyl)-acrylate of boiling point 83°–84° C. (0.4 mbar) are obtained.

EXAMPLE 4

10.2 g (0.1 mole) of ethyl glyoxylate, 10 g (0.1 mole) of ethyl acrylate and 1 g (8.9 millimoles) of DABCO are stirred vigorously for 48 hours at 60° C. Thereafter, volatile components are removed under reduced pressure from a water pump, the residue is taken up in 50 ml of diethyl ether, the resulting solution is washed with 20 ml of 8% strength hydrochloric acid and then 30 ml of water, the organic phase is dried over sodium sulfate, the solvent is separated off and the residue is subjected to fractional distillation to give 11 g (54% of theory) of ethyl 2-(1-hydroxycarbethoxymethyl)-acrylate of boiling point 120°–122° C. (0.3 mbar).

When the experiment is carried out in a similar manner using triethylamine instead of DABCO, a yield of 34% of theory is obtained.

EXAMPLE 5

20.4 g (0.2 mole) of ethyl glyoxylate, 10.6 g (0.2 mole) of acrylonitrile and 2 g (17.8 millimoles) of DABCO are stirred thoroughly for 70 hours at 25° C. The mixture is worked up by a method similar to that described under Example 2, and the residue is subjected to fractional distillation. 17 g (51% of theory) of 2-(1-hydroxycarbethoxymethyl)-acrylonitrile are obtained in the form of a colorless liquid at 105°–107° C. under 0.5 mbar.

EXAMPLE 6

51 g (0.5 mole) of ethyl glyoxylate, 58 g (0.5 mole) of hydroxyethyl acrylate and 5 g (44.6 millimoles) of DABCO are mixed with 100 ml of absolute acetonitrile, and the resulting solution is stirred for 70 hours at 25° C. The mixture is worked up by a method similar to that described under Example 2. 63 g (58% of theory) of hydroxyethyl 2-(1-hydroxycarbethoxymethyl)-acrylate are obtained as a pale yellow oil.

EXAMPLE 7

51 g (0.5 mole) of ethyl glyoxylate, 85.5 g (0.5 mole) of N,N-diethylaminoethyl acrylate and 5 g (62.5 millimoles) of DABCO in 100 ml of absolute dioxane are reacted by a method similar to that described in Example 6. 74 g (54% of theory) of diethylaminoethyl 2-(1-hydroxycarbethoxymethyl)-acrylate are obtained.

We claim:
1. A compound of the formula

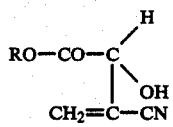

where R is $C_1$–$C_{18}$-alkyl.
2. The compound of claim 1 which is 2-(1-hydroxycarbethoxymethyl)-acrylonitrile.

* * * * *